(12) United States Patent
Cho et al.

(10) Patent No.: US 7,524,292 B2
(45) Date of Patent: Apr. 28, 2009

(54) METHOD AND APPARATUS FOR DETECTING RESPIRATORY DISTURBANCES

(75) Inventors: Yong K. Cho, Maple Grove, MN (US); Steven L. Ning, Fridley, MN (US); Luc R. Mongeon, Minneapolis, MN (US); Scott W. Davie, Saint Paul, MN (US); Todd J. Sheldon, North Oaks, MN (US); Mark K. Erickson, Brooklyn Park, MN (US); H. Toby Markowitz, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/565,092

(22) Filed: Nov. 30, 2006

(65) Prior Publication Data

US 2007/0167843 A1    Jul. 19, 2007

Related U.S. Application Data

(62) Division of application No. 10/419,467, filed on Apr. 21, 2003, now Pat. No. 7,160,252.

(51) Int. Cl.
*A61B 5/08* (2006.01)
*A61B 5/02* (2006.01)
*A61B 5/00* (2006.01)
*A61B 5/103* (2006.01)
*A61B 5/05* (2006.01)

(52) U.S. Cl. .................. 600/529; 600/484; 600/483; 600/536; 600/324; 600/509; 600/595; 600/547

(58) Field of Classification Search ............... 600/484, 600/483–486, 481, 504–506, 529, 536, 547, 600/323–325, 488, 509, 595; 607/17–26
See application file for complete search history.

(56) References Cited

U.S. PATENT DOCUMENTS

| 4,373,527 | A |   | 2/1983  | Fischell        |         |
|-----------|---|---|---------|-----------------|---------|
| 4,485,813 | A |   | 12/1984 | Anderson et al. |         |
| 4,765,340 | A | * | 8/1988  | Sakai et al.    | 600/324 |
| 4,901,725 | A |   | 2/1990  | Nappholz et al. |         |
| 5,329,931 | A | * | 7/1994  | Clauson et al.  | 600/323 |
| 5,385,144 | A | * | 1/1995  | Yamanishi et al.| 600/330 |

(Continued)

FOREIGN PATENT DOCUMENTS

WO    WO01070103 A2    9/2001

*Primary Examiner*—Charles A Marmor, II
*Assistant Examiner*—Navin Natnithithadha
(74) *Attorney, Agent, or Firm*—Stephen W. Bauer

(57) ABSTRACT

A system and method for monitoring respiration including sensing a signal that varies with respiration, deriving a respiration parameter, applying criteria for detecting a respiration disturbance and determining one or more respiratory disturbance metrics. The system preferably includes an implantable sensor with an associated implantable medical device such that chronic respiration monitoring is possible. The implantable medical device may execute methods for detecting and measuring respiratory disturbances or may store data to be transferred to an external device for detecting and measuring respiratory disturbances. Respiratory disturbance detection may trigger a responsive action such as physiological data storage, a change in therapy delivery, or a clinician warning. Assessment of cardiac function may be made based on metrics of respiratory disturbances or a measure of circulatory delay time following detection of a respiratory disturbance.

21 Claims, 8 Drawing Sheets

U.S. PATENT DOCUMENTS

| | | | |
|---|---|---|---|
| 5,398,682 A * | 3/1995 | Lynn | 600/335 |
| 5,507,785 A | 4/1996 | Deno | |
| 5,535,752 A | 7/1996 | Halperin et al. | |
| 5,540,733 A | 7/1996 | Testerman et al. | |
| 5,562,712 A | 10/1996 | Steinhaus et al. | |
| 5,605,151 A * | 2/1997 | Lynn | 600/323 |
| 5,682,877 A * | 11/1997 | Mondry | 128/204.23 |
| 5,738,102 A | 4/1998 | Lemelson | |
| 5,758,652 A | 6/1998 | Nikolic | |
| 5,891,023 A * | 4/1999 | Lynn | 600/323 |
| 5,980,463 A | 11/1999 | Brockway et al. | |
| 5,987,352 A | 11/1999 | Klein et al. | |
| 6,024,704 A | 2/2000 | Meador et al. | |
| 6,044,297 A | 3/2000 | Sheldon et al. | |
| 6,064,910 A | 5/2000 | Andersson et al. | |
| 6,126,611 A | 10/2000 | Bourgeois et al. | |
| 6,162,180 A | 12/2000 | Miesel et al. | |
| 6,223,064 B1 * | 4/2001 | Lynn et al. | 600/324 |
| 6,299,582 B1 | 10/2001 | Brockway et al. | |
| 6,325,761 B1 | 12/2001 | Jay | |
| 6,334,071 B1 | 12/2001 | Lu | |
| 6,342,039 B1 * | 1/2002 | Lynn et al. | 600/529 |
| 6,363,270 B1 * | 3/2002 | Colla et al. | 600/324 |
| 6,454,719 B1 | 9/2002 | Greenhut | |
| 6,471,689 B1 | 10/2002 | Joseph et al. | |
| 6,529,752 B2 * | 3/2003 | Krausman et al. | 600/323 |
| 6,641,542 B2 * | 11/2003 | Cho et al. | 600/529 |
| 6,748,252 B2 * | 6/2004 | Lynn et al. | 600/323 |
| 6,760,608 B2 * | 7/2004 | Lynn | 600/324 |
| 6,811,538 B2 * | 11/2004 | Westbrook et al. | 600/529 |
| 6,830,548 B2 * | 12/2004 | Bonnet et al. | 600/529 |
| 6,839,581 B1 * | 1/2005 | El-Solh et al. | 600/324 |
| 6,881,192 B1 * | 4/2005 | Park | 600/529 |
| 7,160,252 B2 * | 1/2007 | Cho et al. | 600/484 |
| 7,177,686 B1 * | 2/2007 | Turcott | 607/23 |
| 7,206,636 B1 * | 4/2007 | Turcott | 607/17 |
| 7,207,947 B2 * | 4/2007 | Koh et al. | 600/529 |
| 7,297,119 B2 * | 11/2007 | Westbrook et al. | 600/529 |

* cited by examiner

METHOD AND APPARATUS FOR DETECTING RESPIRATORY DISTURBANCES

CROSS REFERENCE TO RELATED APPLICATIONS

This patent application is a divisional application of U.S. Ser. No. 10/419,467, filed Apr. 21, 2003 now U.S. Pat. No. 7,160,252, entitled "Method and Apparatus for Detecting Respiratory Disturbances".

FIELD OF THE INVENTION

The present invention relates to a system and method for chronically monitoring a physiological signal that varies with respiration for detecting respiratory disturbances and determining metrics of such disturbances.

BACKGROUND OF THE INVENTION

Respiratory disturbances are associated with a number of pathological conditions. Cheyne-Stokes respiration is the waxing and waning of respiration associated with congestive heart failure. Kussmaul breathing is rapid deep breathing associated with diabetic ketoacidosis. Central or obstructive forms of sleep apnea are prevalent in both normal and heart failure populations. Detection of respiratory disturbances, such as Cheyne-Stokes respiration, Kussmaul breathing, apnea or hypopnea episodes associated with obstructive or central sleep apnea or other disordered breathing, may be useful in monitoring a patient's disease status, selecting treatment and monitoring its effectiveness.

Respiratory disturbances in the form of sleep-related disordered breathing may often go undetected in patients suffering from heart failure or sleep apnea. Nocturnal Cheyne-Stokes respiration, a form of central sleep apnea, occurs frequently in patients with chronic heart failure. The presence of sleep apnea significantly worsens the prognosis for a heart failure patient. A method for determining the cardiac condition of a patient by a cardiac monitor using the variability of a respiration parameter is generally disclosed in U.S. Pat. No. 6,454,719 issued to Greenhut, incorporated herein by reference in its entirety. Characteristics of periodic breathing patterns, such as hyperpnea length, apnea length, and periodic breathing cycle length, are correlated to circulatory delay time, which is inversely correlated with cardiac output. Therefore, recognizing and monitoring the presence of disordered breathing in heart failure patients could provide useful diagnostic and prognostic information. Moreover, detecting respiratory disturbances and extracting specific parameters related to cardiac function could provide valuable information for assessing a patient's cardiac condition and optimizing therapeutic interventions.

A standard diagnostic approach for sleep apnea includes polysomnography, which requires the patient to stay overnight in a hospital for observation, in addition to medical history and screening questionnaires. Polysomnography involves monitoring of multiple parameters including electroencephalography, electromyography, electrocardiography, oximetry, airflow, respiratory effort, snoring, body position and blood pressure. Polysomnography measures a patient's respiratory patterns during a single sleeping period and is expensive and inconvenient for the patient. Furthermore, a physician must actively prescribe the sleep study and therefore must already suspect a sleep-related breathing disorder. Chronic monitoring of respiratory disturbances as an alternative to polysomnography, particularly in heart failure patients who have increased risk of morbidity in the presence of sleep apnea, is desirable for detecting unrecognized and unsuspected sleep-related disordered breathing.

Chronic monitoring of respiratory disturbances is also desirable in diabetic patients. Diabetic ketoacidosis may be the first symptom to appear in a person with Type I diabetes. Diabetic ketoacidosis develops when blood is more acidic than body tissues due to the accumulation of ketones in the blood when body fat is metabolized for energy in place of glucose reserves when insulin is not available. Persons having Type II diabetes usually develop ketoacidosis only under conditions of severe stress. Recurrent episodes of ketoacidosis in diabetic persons are generally the result of poor compliance with dietary restrictions or self-administered treatments. Kussmaul breathing is a common symptom of ketoacidosis. Therefore early detection and monitoring of Kussmaul breathing in diabetic patients may be valuable in the effective control of diabetes. Kussmaul breathing is typically characterized by relatively deep breathing Respiratory monitoring may be a preferred method for monitoring diabetic status in combination with or in place of periodically measuring blood glucose, which requires the use of hollow needles with associated pain and risks of infection.

Respiration may be measured directly using, for example, external breathing masks. Breathing masks, however, are generally not well tolerated by patients for extended periods of time. A system having one or more sensors disposed at or near the surface of a patient's body for monitoring physiological variables of a patient in real time, including respiratory sounds for the detection of abnormal breathing patterns, is generally disclosed in U.S. Pat. No. 5,738,102 issued to Lemelson.

A system for monitoring respiration using an implantable sensor would allow chronic, ambulatory monitoring for respiratory disturbances. Impedance measurements made using implanted electrodes may be used for detecting changes in thoracic impedance associated with changing lung volume during inspiration and expiration. Tidal volume and respiration rate may be determined from the measured impedance. Minute ventilation may then be calculated from the extracted tidal volume and respiration rate. Normal changes in minute ventilation in response to exercise are measured using impedance sensing in some cardiac pacemakers in order to provide a sensor-indicated pacing rate for rate-responsive cardiac pacing. See, for example, U.S. Pat. No. 4,901,725 issued to Nappholz.

Respiratory signals may be extracted from other physiological signals that can be obtained from implantable sensors. Other physiological signals, such as subcutaneous ECG, cardiac electrogram (EGM), blood pressure, and heart sound signals, typically contain cyclical amplitude changes due to the influence of the respiratory cycle. Pulsus paradoxus refers to a decrease in arterial blood pressure that occurs during inspiration. A device for measuring pulsus paradoxus for assessing and monitoring patients with respiratory disease is generally disclosed in U.S. Pat. No. 6,325,761 issued to Jay, incorporated herein by reference in its entirety. A method for computing tidal volume as a function of extracted blood pressure information indicative of the change in blood pressure that occurs over a respiratory cycle is generally disclosed in U.S. Pat. No. 5,980,463, issued to Brockway, et al., incorporated herein by reference in its entirety. Implantable cardiac rhythm management or cardiac monitoring devices may sense ECG, EGM, blood pressure and/or other physiological signals that are variable due to the influence of respiration. Thus, an opportunity exists for detecting changes in respiration rate using physiological signals already sensed by an implantable device without having to introduce new sensors.

It is desirable to provide a system and method for detecting and monitoring episodes of respiratory disturbances based on a physiological signal sensed by an implantable sensor, which disturbances may be associated with a particular pathological condition. Monitoring of respiratory disturbances may be used for diagnostic or prognostic purposes and may further be used for triggering other types of patient monitoring or the delivery of a desired therapy.

SUMMARY OF THE INVENTION

The present invention provides a system and method for monitoring a patient's respiration for the purposes of detecting respiratory disturbances related to a pathological condition. A system includes an implantable sensor in association with an implanted device. The implantable sensor provides a signal that varies with the respiration cycle such that at least a respiration rate, and optionally other respiration features, may be derived or extracted from the sensed signal. Digitized signal data is provided as input to a respiratory disturbance detection algorithm. The detection algorithm detects a respiratory disturbance when measured respiration parameters meet predetermined detection criteria such as an apnea or hyponea threshold. The detection algorithm may be implemented in the internal device, which may respond to a respiratory disturbance detection by delivering a therapy or collecting and storing physiological data relating to the respiration signal and/or other physiological signals sensed by the implanted device. In an alternative embodiment, the detection algorithm may be implemented in an external device. Digitized signal data may be stored in the implanted device and uplinked to the external device for post-processing and detection of respiratory disturbances. Detected respiration disturbances may be flagged and physician alert generated.

Metrics of detected respiratory disturbances may be made and tracked over time to monitor worsening or improvement of the disordered breathing condition. Preferred metrics include apnea length, hyperpnea length, periodic breathing cycle length, and number of disturbances detected. An additional assessment of cardiac function may be made based on these metrics and/or by determining a "circulatory delay time" based on detection of respiratory disturbances and monitoring blood oxygen saturation. Circulatory delay time (CDT), which is correlated inversely to cardiac output, may be determined as the time from the end of an apnea, hypopnea or the beginning of a hyperpnea episode to the subsequent minimum in oxygen saturation. The reader should note that typically a apnea-hyperpnea cycle and the nearly-sinusoidal SaO2 signal are usually slightly out of phase, so minimum SaO2 (e.g., due to apnea) occurs during a hyperpnea event window and a peak SaO2 (e.g., due to subsequent hyperpnea) occurs during an adjacent apnea event window. Thus, CDT can not only be measured from the beginning of hyperpnea period to min SaO2, but can be estimated by measuring the time from the beginning of hyperpnea to max SaO2. In one embodiment, an implantable oximeter may be used in association with the implantable device. In an alternative embodiment, an external oximeter may be used with the oxygen saturation signal communicated to the implantable device by telemetry for determination of circulatory delay time. Circulatory delay time and metrics of respiratory disturbances can be useful in indirectly monitoring cardiac function.

A system and method provided in accordance with the present invention allow respiratory disturbances associated with a pathologic condition to be detected based on sensing a physiological signal using an implantable sensor. Such chronic, ambulatory monitoring of respiration allows prompt recognition of changes or worsening of a patient's condition, even through remote monitoring, making early intervention and treatment possible.

DETAILED DESCRIPTION OF THE INVENTION

Figure 1:
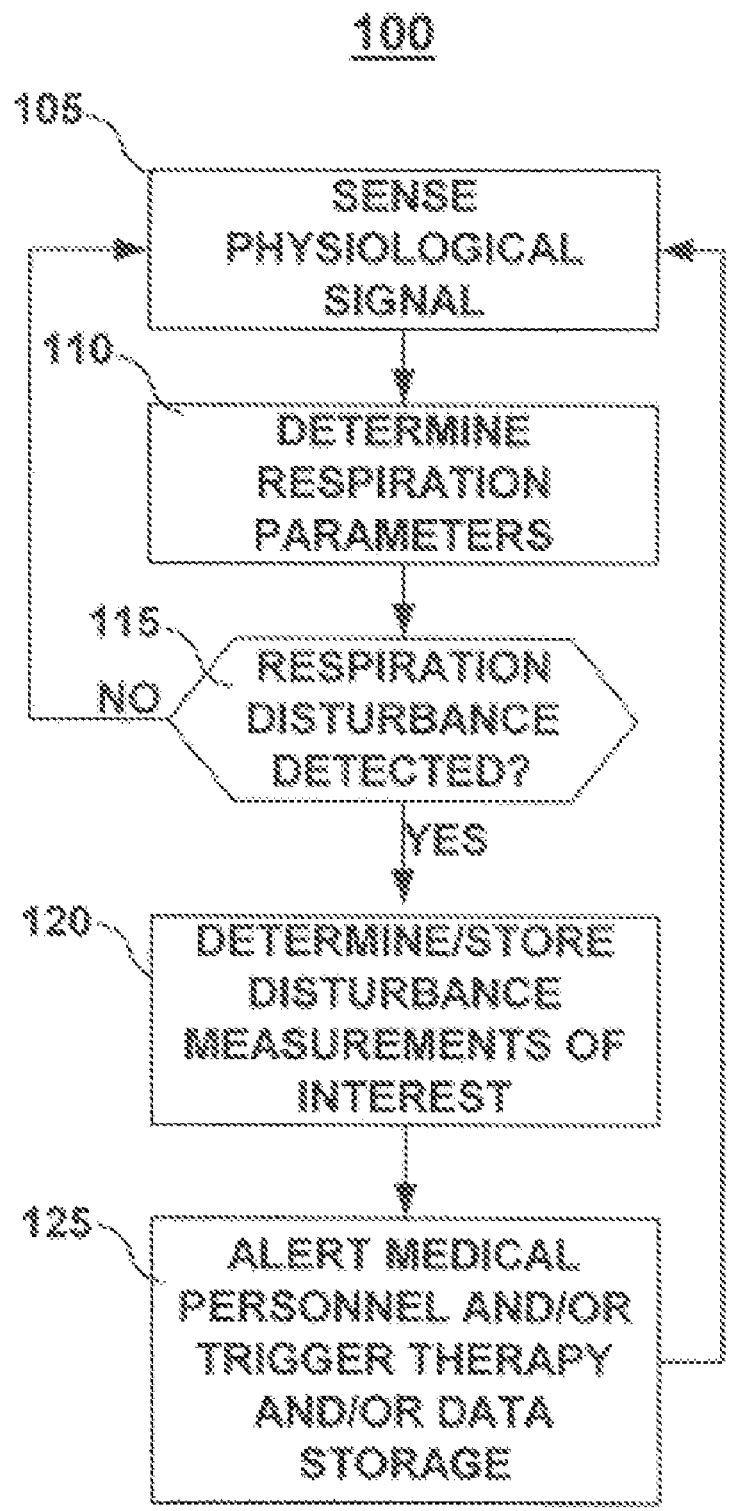
FIG. 1 is a flow chart providing an overview of methods included in the present invention for detecting a respiratory disturbance.

As indicated above, the present invention is directed at providing a system and method for chronically monitoring respiration for pathological respiratory disturbances. Respiratory disturbances may be associated with obstructive or central sleep apnea, Cheyne-Stokes breathing, Kussmaul breathing, asthma, and Cystic fibrosis or other types of disordered breathing patterns. Such breathing patterns, particularly sleep apnea and nocturnal Cheyne-Stokes breathing, may go undetected without chronic monitoring. FIG. 1 is a flow chart providing an overview of methods included in the present invention for detecting a respiratory disturbance.

At step 105, a physiological signal that varies with a patient's respiration cycle is monitored. Monitoring may be continuous or on a periodic or triggered basis. In a preferred embodiment, an implantable sensor in association with an implantable medical device (IMD) is used for sensing a physiological signal. As will be described, the IMD is provided for processing and/or storing sensed signal data. A physiological signal received may be a thoracic impedance measurement from which tidal volume and respiration rate may be determined for calculating minute ventilation. A physiological signal may alternatively be an ECG, EGM, blood pressure, activity sensor, oximeter or other sensor signal that includes variations due to the respiratory cycle.

As will be described in greater detail later in conjunction with FIG. 7, the remainder of method 100 may be implemented in the implantable device or in an external device capable of receiving sensed signal data from the implanted device via a telemetric communication link. At step 110, parameters indicative of the patient's respiratory activity are derived from the sensed signal. Preferably, at least a respiration rate is determined at step 110. Additionally, other respiration parameters, such as tidal volume or peak amplitudes associated with the respiration cycle, may be determined.

At decision step 115, the respiration parameters determined at step 110 are compared to predetermined criteria for detecting a respiratory disturbance. Such criteria may include at least a respiration rate or minute ventilation criterion such that when the respiration rate or minute ventilation is less than or greater than a normal range or crosses a detection threshold, a respiratory disturbance is detected at decision step 115.

At step 120, measurements of the respiratory disturbance are determined and stored. Such measurements preferably include at least the duration of the disturbance. At step 125, detection of the respiratory disturbance may optionally trigger a warning to medical personnel, the delivery of a therapy, and/or the storage of physiological data in the implanted device.

Figure 2:
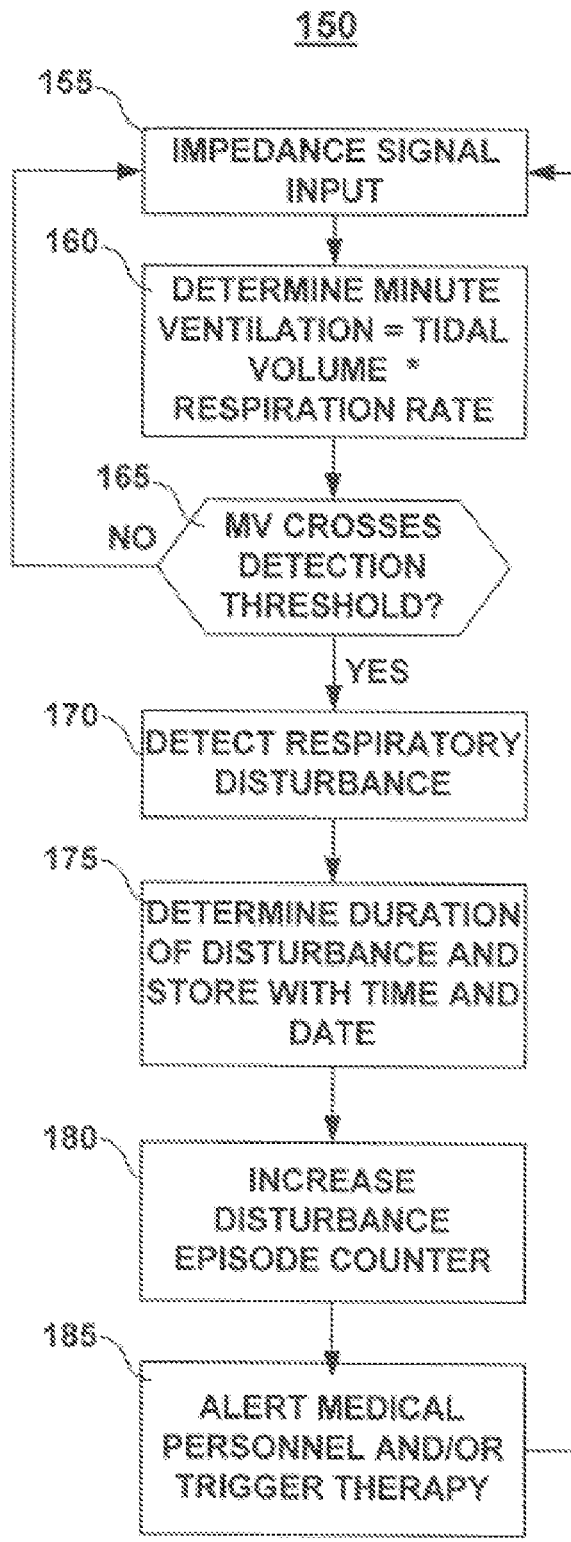
FIG. 2 is a flow chart summarizing steps included in one embodiment of the present invention for monitoring respiratory disturbances based on impedance sensing.

FIG. 2 is a flow chart summarizing steps included in one embodiment of the present invention for monitoring respiratory disturbances based on impedance sensing. Monitoring of minute ventilation (designated "MV" in FIG. 2) using a thoracic impedance measurement is known for use in rate responsive cardiac pacing. At step 155 of method 150, a thoracic impedance signal is received, and at step 160 the tidal volume and respiration rate are derived from the impedance signal, which may be used for calculating minute ventilation. For the purposes of the present invention, any method known in the art for measuring an impedance and deriving minute ventilation may be used. In a preferred embodiment, minute ventilation measurement is performed according to the methods employed by the commercially available Medtronic Kappa® 400 Pacing System and equivalent systems. In addition, for respiration disturbance measurements, the data does not have to be converted to MV. If one measures respiration using an impedance sensor without converting the signal to MV, it is still acceptable. The entire minute ventilation determination methodology of the Kappa 400 Pacing System is retained in the disclosed embodiment of the present invention. Various alternative methods and apparatus for measuring a patient's minute ventilation in rate-responsive pacemakers are generally disclosed in U.S. Pat. No. 6,334,071 issued to Lu, U.S. Pat. No. 5,562,712 issued to Steinhaus et al., U.S. Pat. No. 5,507,785 issued to Deno, and the above-cited U.S. Pat. No. 4,901,725 issued to Nappholz et al., all of which patents are hereby incorporated herein by reference in their entirety.

At decision step 165, one or more predetermined criterion for detecting a respiratory disturbance are applied to the calculated minute ventilation (MV), and/or the measured tidal volume and/or respiration rate. Predetermined criteria may include comparing a given respiration parameter to a minimum or maximum threshold. If criteria for determining a respiratory disturbance are not satisfied, the method 150 returns to step 155 to continue monitoring the impedance signal. If detection criteria are met at step 165, a respiratory disturbance is detected at step 170.

Measurements of the disturbance may then be made, preferably including at least the duration of the disturbance as indicated at step 175. The duration of the disturbance may be an apnea/hypopnea length or hyperpnea length determined as the number of device clock or timer cycles during which corresponding detection criteria are satisfied. The duration is stored at step 175, preferably along with a time and date label to indicate when the detection was made. At step 180, a counter for tracking the number of detected respiratory disturbance episodes is increased by one.

An optional warning to medical personnel by an external device or triggering of a therapy delivery or data storage by an internal device may be generated at step 185. A triggered therapy may be, but is not limited to, cardiac pacing, delivery of a pharmacological agent, insulin delivery, stimulation of the upper airway muscles, the diaphragm, or other electrical stimulation of the central nervous system, peripheral nerves or smooth or skeletal muscle. The method 150 is preferably repeated to continue monitoring for respiratory disturbances by returning to step 155.

Figure 3:
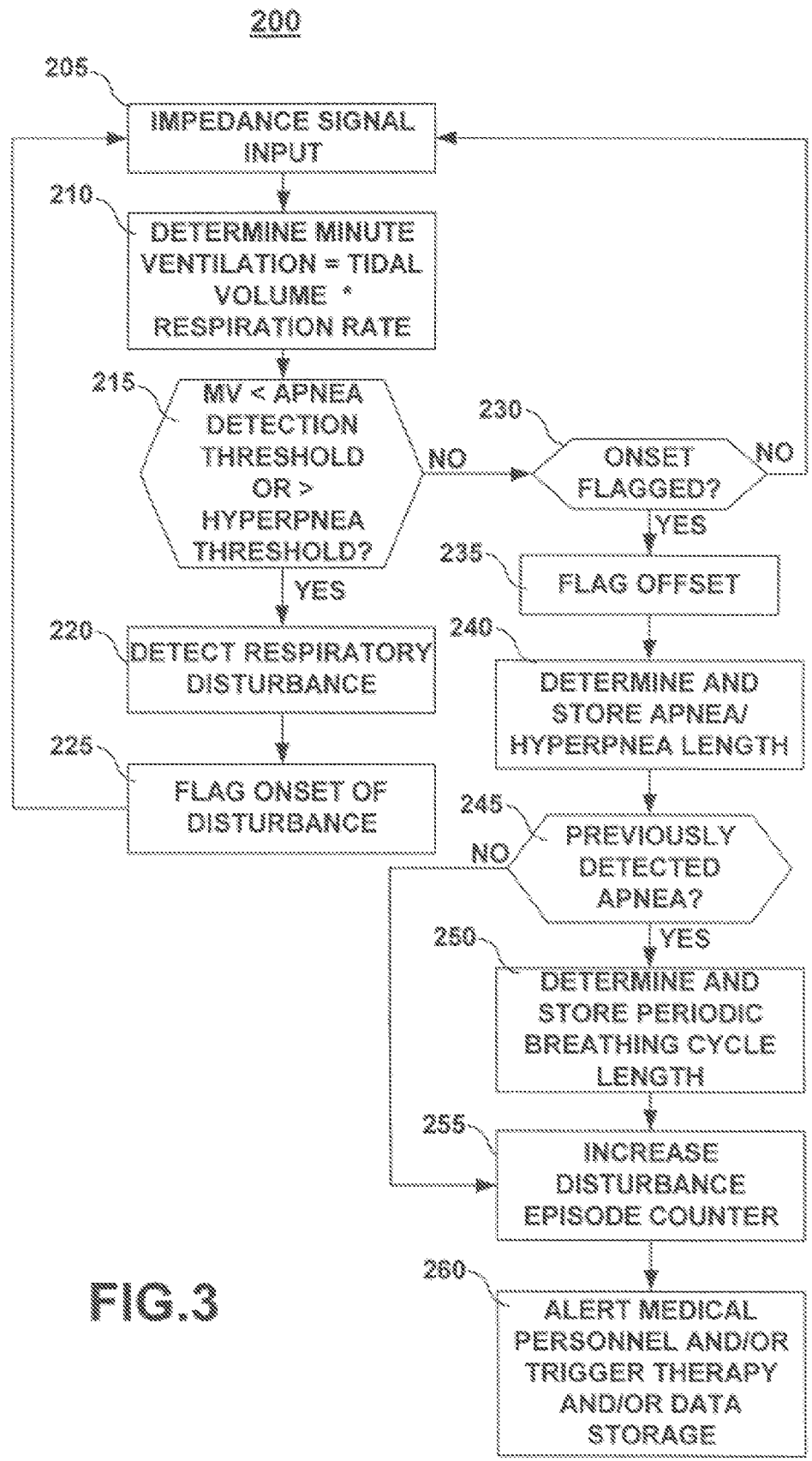
FIG. 3 is a flow chart providing additional details regarding methods for determining metrics of respiratory disturbances in one embodiment of the present invention.

FIG. 3 is a flow chart providing additional details regarding methods for determining metrics of respiratory disturbances in one embodiment of the present invention. Upon detecting a respiratory disturbance, it may be desirable to determine various metrics of the disturbance in order to assess the severity of the disturbance and/or track changes in these metrics over time as a way of assessing relative improvement or worsening of the associated pathological condition. In method 200, an impedance signal input is received at step 205 and used for determining minute ventilation, at step 210, based on derived tidal volume and respiration rate. At step 215, the minute ventilation ("MV" in FIG. 3) (or alternatively the derived tidal volume or respiration rate) is compared to a predetermined apnea detection threshold and hyperpnea detection threshold. If a threshold crossing is detected, a respiratory disturbance is detected at step 220, and the time of the onset of the disturbance is flagged at step 225.

Method 200 then returns to step 205 and continues to monitor the respiration parameters until the detection criterion is no longer satisfied at decision step 215. If a respiratory disturbance onset has been flagged, as determined at decision step 230, the respiratory disturbance offset is now flagged at step 235. If the detection criterion is not satisfied at step 215, and no onset is flagged as determined at step 230, then method 200 returns to step 205 to continue monitoring respiration parameters. After flagging the onset and offset of an apnea or hyperpnea period, the length of the apnea or hyperpnea period is stored at step 240 as the difference between the flagged onset and offset.

At step 245, method 200 determines if a previous apnea episode has been recently detected, which could indicate the presence of a repetitive breathing pattern. Repetitive apnea-hyperpnea or hypopnea-hyperpnea alternation is typical of certain pathological breathing patterns such as sleep apnea and Cheyne-Stokes breathing. If decision step 245 is affirmative, a periodic breathing cycle length is determined and stored at step 250 as the time between the onset of two consecutively detected apnea episodes. At step 255, a respiratory disturbance episode counter may be increased by one for each disturbance detected. Depending on the type of pathological breathing pattern being monitored, a disturbance that would increase the episode counter may be a single apnea, hypopnea, or hyperpnea event or may be a complete apnea-hyperpnea or hypopnea-hyperpnea cycle. At optional step 260, a warning to alert medical personal and/or a therapy delivery and/or data storage trigger may be generated.

Figure 4A:
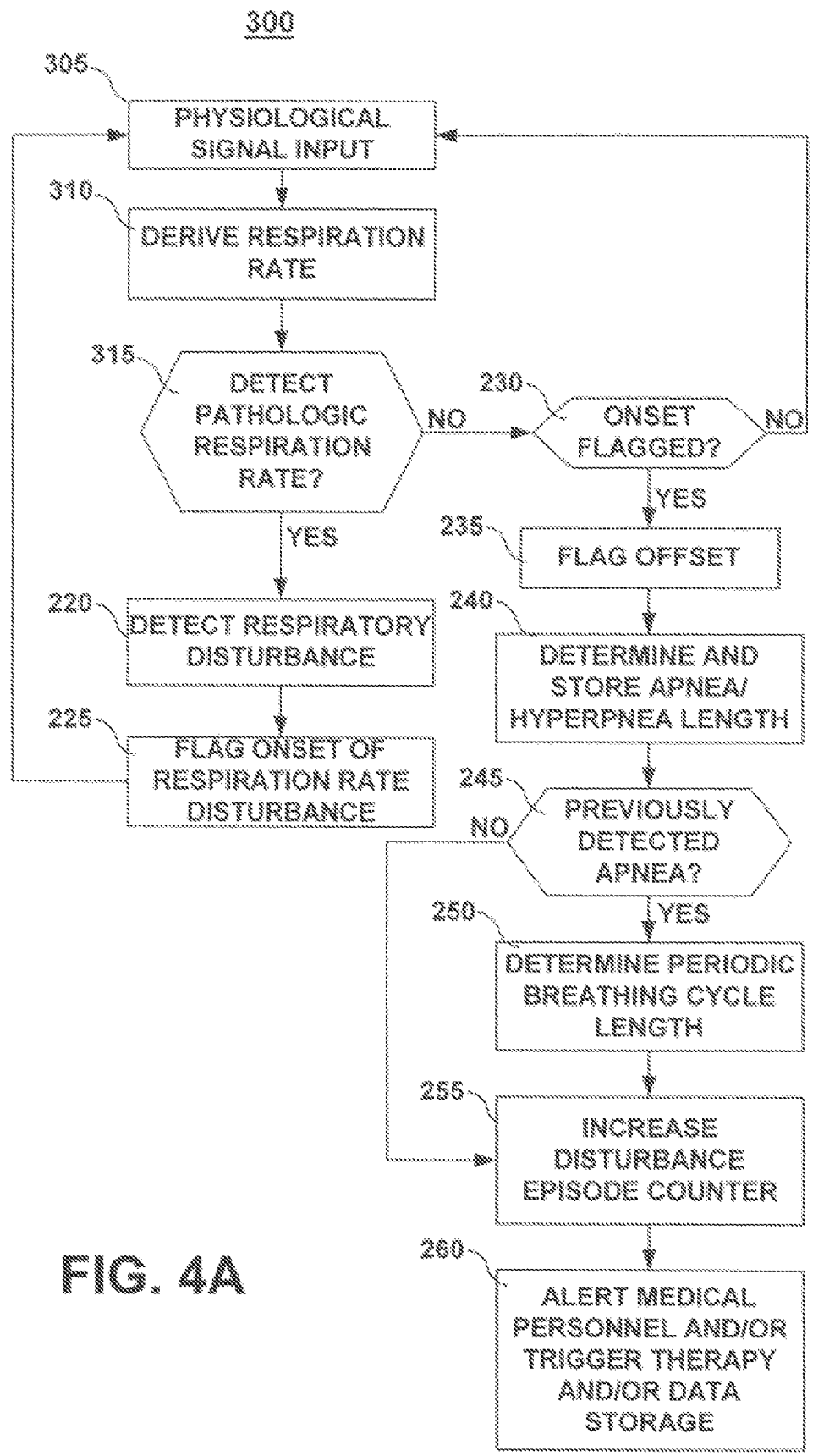
FIG. 4A is a flow chart summarizing steps included in an alternative embodiment of a method for monitoring for respiratory disturbances.

FIG. 4A is a flow chart summarizing steps included in an alternative embodiment of a method for monitoring for respiratory disturbances. Alternative embodiments may detect pathologic breathing patterns by determining a patient's respiration rate from any physiological signal that includes variations due to the influence of inspiration and expiration. At step 305, a physiological signal input is received. A physiological signal that includes respiration related variations may be, but is not limited to, an ECG signal, an EGM signal, a blood pressure signal, an activity sensor signal, heart sounds, or an oxygen saturation signal. Various implantable sensors are known for use with implantable medical devices. Examples of implantable sensors that are believed to be appropriate for use with the present invention for deriving respiration parameters are: an absolute blood pressure sensor as generally disclosed in U.S. Pat. No. 6,024,704 issued to Meador et al. or U.S. Pat. No. 5,535,752 issued to Halperin et al.; a piezoelectric activity sensor as generally disclosed in U.S. Pat. No. 4,485,813 issued to Anderson et al.; and an oxygen sensor generally disclosed in U.S. Pat. No. 6,162,180 issued to Miesel et al., all of which patents are incorporated herein by reference in their entirety.

At step 310, the patient's respiration rate is derived from the physiological signal. Generally, by filtering a sensed signal to remove higher frequency components and pass low frequencies associated with the respiration cycle, a respiration rate may be determined. A preferred method for deriving the respiration rate comprises a simple peak detection algorithm. In this case, an input impedance signal measures the thoracic excursion due to respiration (e.g., herein "respiration"). By detecting individual breaths and related peaks and valleys of the imput impedance signals, respiration rate can be derived (by measuring interval between peaks) or tidal volume (by measuring peak to peak amplitude change from a peak to the corresponding valley). One method for deriving a respiration rate from a blood pressure signal that may be adapted for use with the present invention is generally disclosed in U.S. Pat. No. 6,299,582 issued to Brockway et al., incorporated herein by reference in its entirety. A method for determining respiration rate and/or depth from sensed heart sound is generally disclosed in U.S. Pat. No. 6,064,910 issued to Andersson et al., incorporated herein by reference in its entirety. The derived respiration rate is compared to predetermined criteria for detecting a pathologic respiration rate at decision step 315. For example, predetermined respiration rate criteria may define a rate limit or zone that is indicative of Kussmaul breathing (which is more closely related to tidal volume), Cheyne-Stokes breathing, apnea, asthma, or other respiratory disturbances.

Identically numbered steps 220 through 260 correspond to those in method 200 of FIG. 3 described above. Briefly, the onset and offset of a detected respiratory disturbance are flagged (steps 225 and 235, respectively) allowing the duration of the disturbance (step 240) and the cycle length of a periodic breathing cycle (step 250) to be determined (and optionally stored at step 250). A respiratory disturbance episode counter is increased (step 255), and a responsive action may be taken (step 260).

Figure 4B:
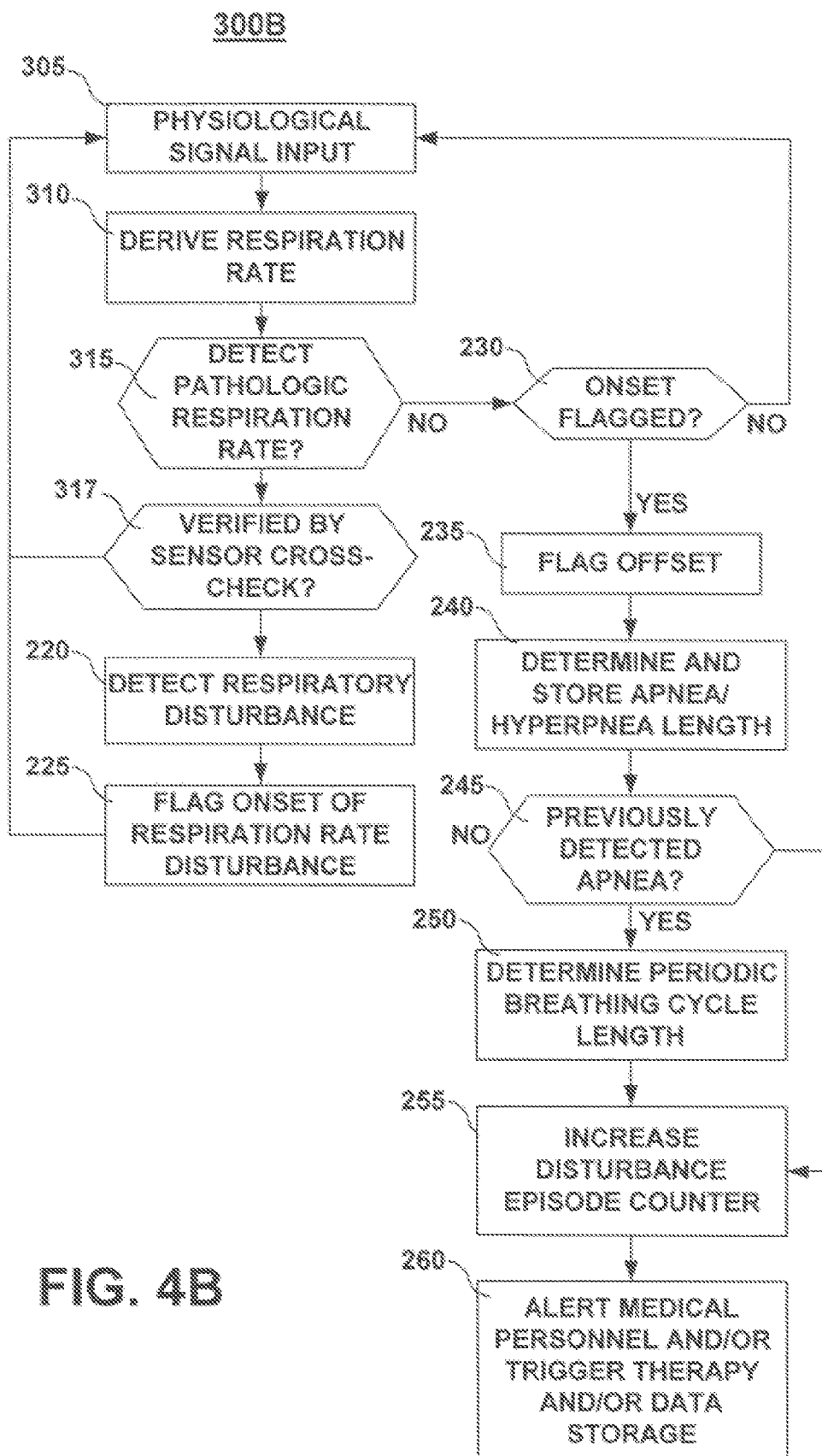
FIG. 4B is a flow chart summarizing steps included in an alternative embodiment of a method for monitoring for respiratory disturbances that includes a sensor cross-check.

FIG. 4B is a flow chart summarizing steps included in an alternative embodiment of a method for monitoring for respiratory disturbances that includes a sensor cross-check. Identically numbered steps in FIG. 4B correspond to those in FIG. 4A, however in method 300B an additional sensor-cross check step 317 is included for verifying a suspected respiratory disturbance prior to detecting the disturbance at step 220. A sensor cross-check may employ the signal from an additional sensor or sensors for verifying that modulation of the primary physiological signal used to detect the respiratory disturbance is indeed due to respiration and not other motion or factors. In one embodiment, the signal from a body posture sensor may be used to verify that the signal variations extracted from the primary signal are not due to changes in body motion. An appropriate posture sensor is generally described in U.S. Pat. No. 6,044,297 issued to Sheldon, et al., incorporated herein by reference in its entirety. Also, at step 250 the cycle length of a periodic breathing cycle to be determined and stored (although not specified in the text accompanying step 250).

Figure 5:
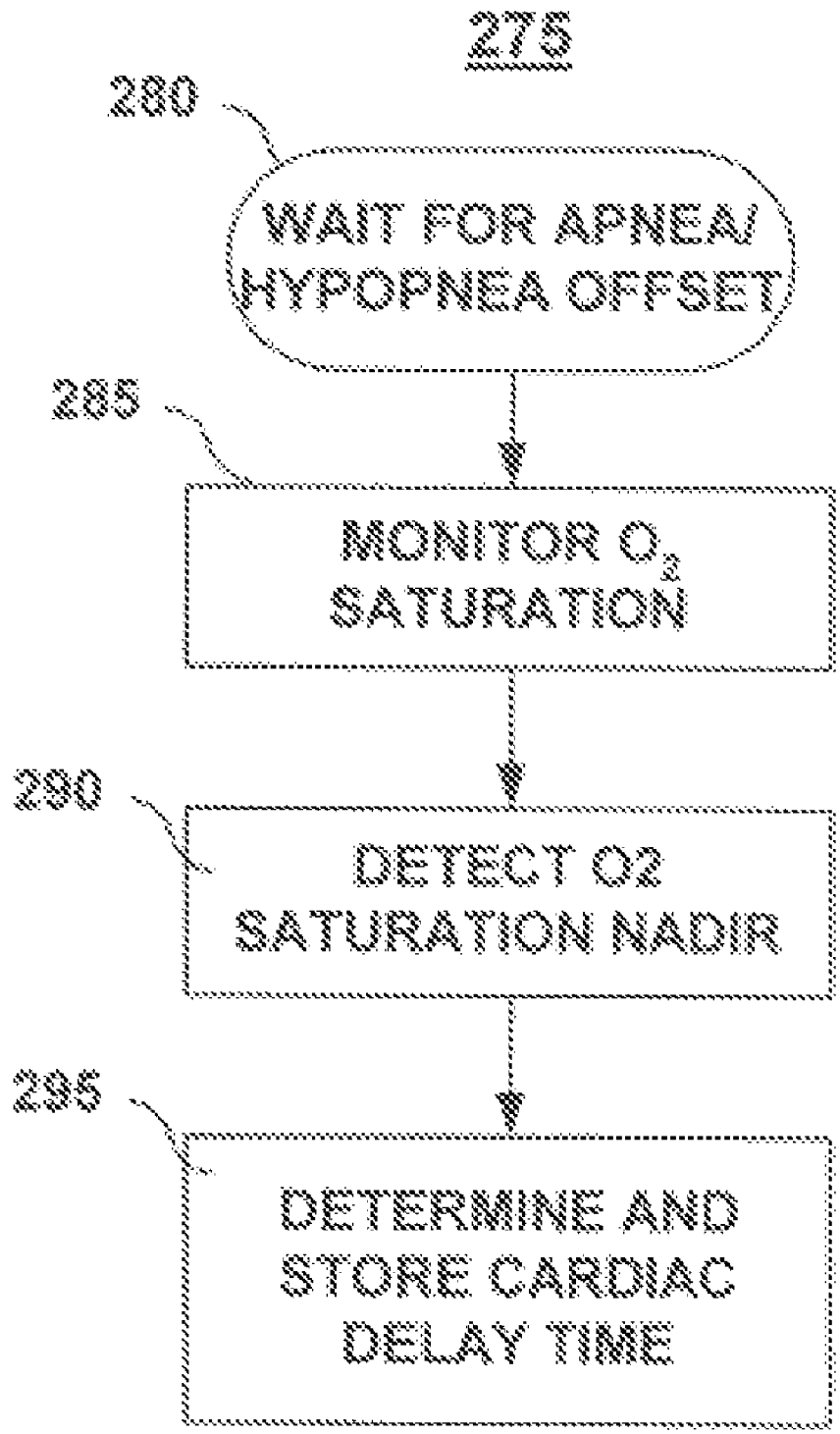
FIG. 5 is a flow chart summarizing an additional feature for determining a "circulatory delay time" that may be included in methods for monitoring for respiratory disturbances in a heart failure patients.

FIG. 5 is a flow chart summarizing an additional feature for determining a "circulatory delay time" (CDT) that may be included in methods for monitoring for respiratory disturbances in a heart failure patients. As noted above, heart failure patients may often experience sleep apnea or Cheyne-Stokes breathing. Monitoring such periodic breathing patterns offers the opportunity to assess the patient's cardiac output indirectly by measuring the circulatory delay time. Circulatory delay time, which is correlated inversely to cardiac output, is the time between the end of an apnea or hypopnea period and the subsequent minimum blood oxygen saturation (or, conversely, the end of a hyperpnea period and the subsequent maximum blood oxygen saturation). However, for some situations this statement of a converse is not completely true. That is, maximum SaO2 (or normal SaO2 in this case) can be achieved if hyperpnea period is adequately long. If one has a long hyperpnea period, SaO2 can return to normal (peak is achieved) without "offset" of hyperpnea period. If apnea-hyperpnea is compared to SaO2 (of tissue perfusion), apnea can be thought of as ligation of major vessel and hyperpnea as "reperfusion." So, CDT is time between the beginning of a reperfusion at the heart to the beginning of reperfusion at the tissue where measurement is made.

At step 280, the method 275 for measuring circulatory delay time waits for the offset of an apnea or hypopnea episode to be detected according to the methods described above. Oxygen saturation is monitored, as indicated at step 285, until a minimum oxygen saturation is detected at step 290 following the apnea offset. The time between the apnea or hypopnea offset and oxygen saturation nadir is the circulatory delay time, which is determined and stored at step 295. Alternatively, the offset of a hyperpnea episode could be detected at step 280 and the time of the subsequent maximum oxygen saturation detected at step 290 (as above, under certain conditions, this alternative may not be true). As will be described in greater detail below, an implantable or external oximeter for measuring oxygen saturation may be included in the system of the present invention.

Figure 6:
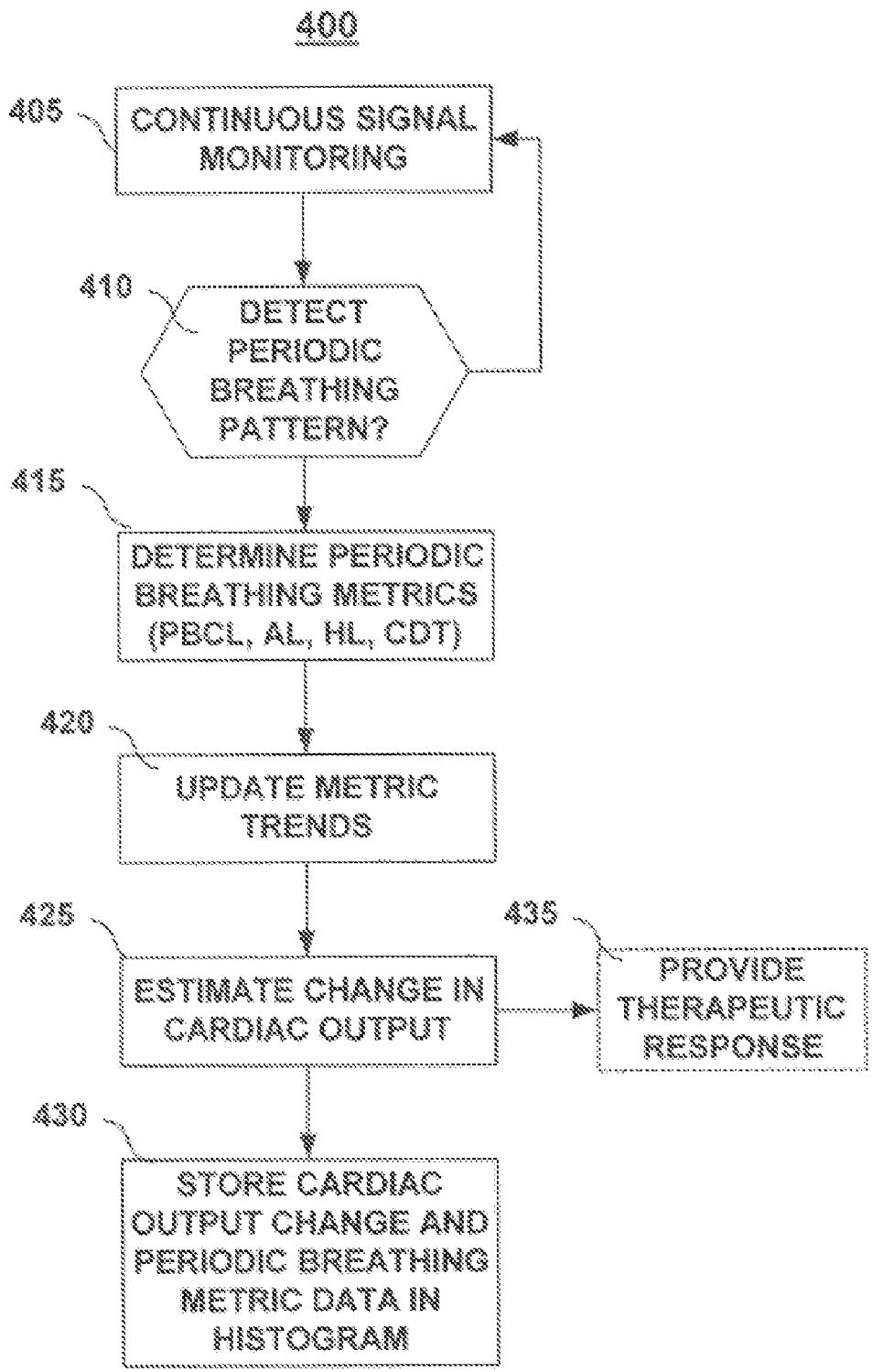
FIG. 6 is a flow chart summarizing steps included in a method for assessing cardiac function from respiratory disturbance metrics.

FIG. 6 is a flow chart summarizing steps included in a method for assessing cardiac function from respiratory disturbance metrics. At step 405, one or more physiological signals are continuously monitored for detecting a respiratory disturbance according to the methods described above. Physiological signals indicative of heart function may additionally be monitored at step 405. If a respiratory disturbance is detected and determined to be a periodic breathing pattern at step 410 based on recent apnea/hypopnea detections, metrics of the periodic breathing pattern are determined at step 415. If not the method returns to step 415 ("continuous signal monitoring"). Metrics preferably include, but are not limited to, periodic breathing cycle length (PBCL), apnea length (AL), hyperpnea length (HL), and circulatory delay time determined as described above in conjunction with FIG. 5. These periodic breathing metrics can be correlated to cardiac function. However, in the event that a SaO2 measurement is not available, CDT can be estimated by measuring hyperpnea length. Underlying hypothesis is that in order to "reperfuse" the oxygen debt, a patient has to hyperventilate (hyperpnea) for a physiologically required time. If the oxygen debt gets worsened (e.g., as in heart failure patients with already compromised cardiac function), the hyperpnea period will be prolonged in order to recoup the debt. Therefore, hyperpnea duration has a higher correlation to heart failure condition than apnea duration.

Trends of these periodic breathing metrics are determined and stored at step 420 such that, at step 425, a change in cardiac output may be estimated based on respiratory disturbance metrics and/or circulatory delay time. At step 430, the estimated cardiac output change and periodic breathing metrics are stored, preferably in a histogram format. These data may be displayed for review by a physician such that worsening or improvement in cardiac condition can be observed. Thus, detection and evaluation of disordered breathing patterns may be used for assessing a patient's cardiac condition. If method 400 is implemented in an implantable device capable of delivering a heart failure therapy, a worsening or improvement in cardiac output, determined at step 425, may optionally automatically trigger an appropriate delivery, withholding, or adjustment of therapy at step 435.

As indicated above, the present invention preferably employs an implantable sensor for chronic respiration monitoring. The methods described above for detecting a respiratory disturbance may be fully incorporated in the implantable medical device in association with the implantable sensor. Alternatively, an algorithm for detecting a respiratory disturbance and measuring characteristics of a respiratory disturbance may be implemented in an external device in telemetric communication with the implanted device associated with the implantable sensor, in which case the implanted device serves primarily, for the purposes of the present invention, for storing chronic sensor signal data.

Figure 7:
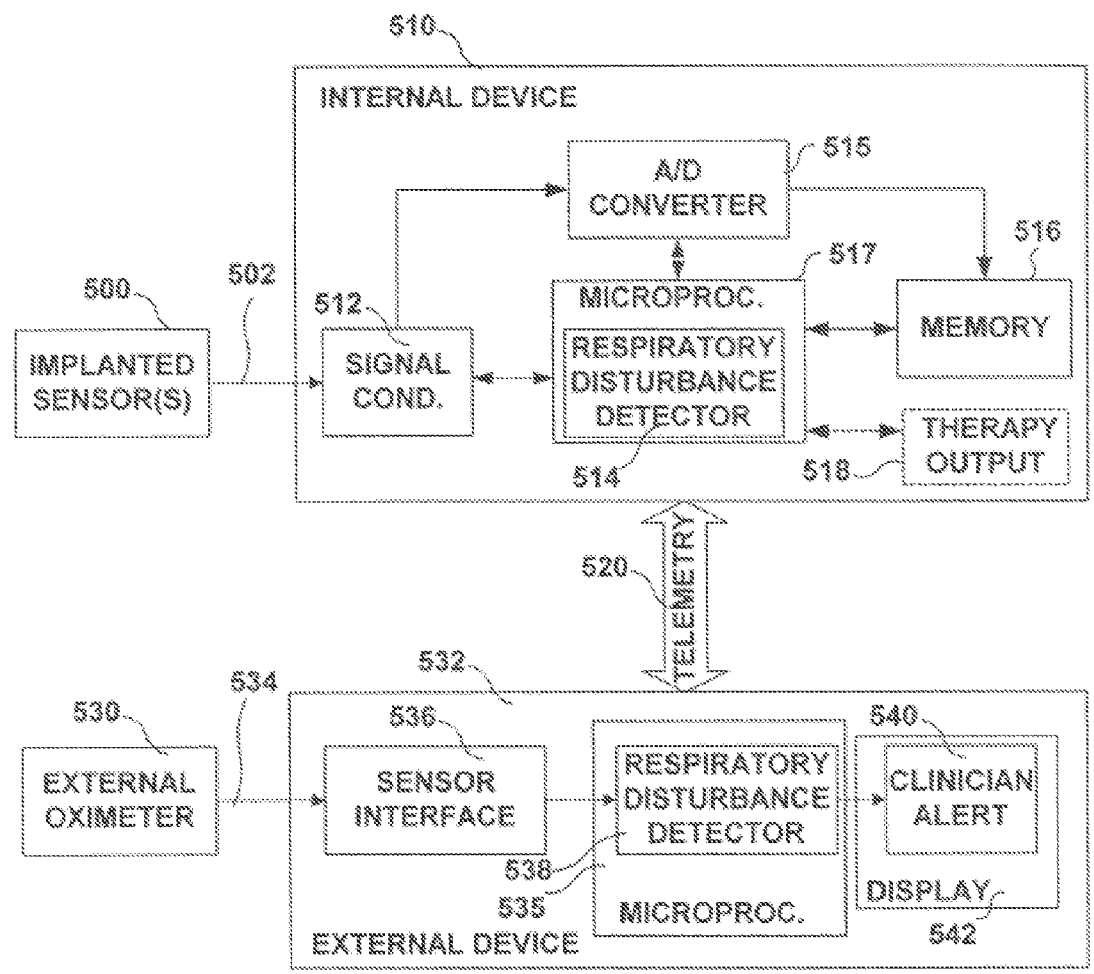
FIG. 7 is a high-level schematic diagram illustrating the implementation of the methods included in the present invention in a system that includes an implantable sensor associated with an implantable device and an external device in telemetric communication with the implanted device.

FIG. 7 is a high-level schematic diagram illustrating the implementation of the methods included in the present invention in a system that includes an implantable sensor associated with an implantable device and an external device in telemetric communication with the implanted device. Implantable sensor(s) 500 provides input via appropriate lead(s) or conductor(s) 502 to signal conditioning circuitry 512 of an internal device 510. Implantable sensor(s) 500 may be located externally to device 510 but within the body of the patient or internally to device 510. Sensor(s) 510 may be electrodes for sensing an ECG, EGM, or diaphragmatic EMG signal, electrodes for sensing thoracic impedance, a blood pressure sensor, an activity sensor, an oxygen sensor, or any other sensor that is expected to provide a variable signal containing information related to a patient's respiration pattern. Multiple sensors containing respiratory information may be included. Depending on the type of implantable device used, additional physiological sensors may be present such as temperature sensors, pH sensors, or any other sensors of signals of interest.

Signal conditioning circuit 512 is provided for filtering, amplifying, rectifying or otherwise conditioning sensor signal input as necessary to eliminate noise and signal components unrelated to respiration. Additional signal conditioning circuitry may be included in device 510 if sensed signals are used for other functions of device 510 other than detection of respiratory disturbances. For example, an ECG signal may be filtered by signal conditioning circuit 512 for extracting a respiration rate, and the ECG signal may be used by other circuitry for detecting the patient's heart rhythm. In another example, a blood pressure signal may be filtered by circuit 512 for deriving a respiration rate, and the blood pressure signal may be used by other circuitry included in device 510 for monitoring a patient's cardiac function.

When respiration disturbance detection methods described herein are incorporated in the internal device 510, the output from signal conditioning circuit 512 is provided as input to an analog-to-digital (A/D) converter 515 which provides input to respiratory disturbance detector 514. Output from A/D converter 515 may also be provided directly to data storage memory 516 for storing digitized signal data that may be uplinked to external device 532 through telemetry link 520. Communication systems for use with implantable devices are known in the art. Detector 514 may perform additional signal processing to derive signal features of interest, such as respiration rate, and perform the methods described above for detecting a pathological respiration pattern. Detector 514 is preferably implemented as programmable software stored in the memory of microprocessor 517. Alternatively, detector 514 may be in the form of dedicated digital circuitry. Microprocessor 517 includes memory for storing executable programs for controlling and executing various device functions.

If a respiratory disturbance is detected by detector 514, according to the methods included in the present invention, other device functions may be triggered such as the storage of physiological data in memory 516 and/or the delivery of a therapy from a therapy output controller 518. Stored data may include measurements of the respiratory disturbance, time and date information relating to when the disturbance was detected, the number of disturbances detected, updated trends of respiratory disturbance metrics, as well as other data based on other sensor input, such as ECG or EGM, blood pressure, oxygen saturation, activity, and so on.

Thus, device 510 may be provided as an implantable recording device capable of monitoring physiological signals and storing physiological data upon a triggering event. Physiological data and respiratory disturbance metrics stored in data storage memory 516 may be uplinked to an external device 532 through telemetry link 520. Stored data may then be displayed on display 542 for review by a physician. Exemplary implantable physiological recording and monitoring devices of this type, in which aspects of the present invention may be implemented, include the Medtronic Reveal® Implantable Loop Recorder, and the Medtronic Chronicle® Implantable Heart Failure Monitor. Internal device 510 and sensor(s) 500 may be a minimally invasive, subcutaneous system. A minimally invasive, sub-cutaneous implant in which aspects of the present invention may be incorporated is generally disclosed in U.S. Pat. No. 5,987,352, issued to Klein et al., incorporated herein by reference in its entirety. Internal device 510 and sensor(s) 500 may alternatively be a relatively more invasive system with sensor(s) 500 implanted submuscularly, intramuscularly, along or within the vascular system, within the thoracic cavity, heart, airways or other internal body locations appropriate for receiving a signal variable with the patient's respiration cycle. A system including a chronically implanted blood pressure sensor and processing element is generally disclosed in U.S. Pat. No. 5,758,652 issued to Nikolic, incorporated herein by reference in its entirety.

If device 510 includes therapy delivery capabilities, a therapy output control 518 may deliver a therapy in response to the detection of a respiratory disturbance. Such therapies may include cardiac pacing, neuromuscular stimulation, stimulation of the central nervous system, delivery of a pharmacological or biological agent, or other therapy. Thus, device 510 may be embodied as a cardiac pacemaker, implantable cardioverter defibrillator (ICD), neuromuscular stimulator or other type of electrical pulse generator, implantable drug delivery device or other type of therapeutic, implantable device. Examples of implantable devices that include therapy delivery capabilities in which aspects of the present invention could be implemented include: a cardiac pacing device for managing sleep apnea generally disclosed in U.S. Pat. No. 6,126,611 issued to Bourgeois et al., a medication infusion system generally disclosed in U.S. Pat. No. 4,373,527 issued to Fischell, an implantable drug delivery system generally disclosed in U.S. Pat. No. 6,471,689 issued to Joseph et al., and a device for stimulating upper airway muscles for treating obstructive sleep apnea generally disclosed in U.S. Pat. No. 5,540,733 issued to Testerman et al., all of which patents are incorporated herein by reference in their entirety.

Thus, aspects of the present invention may be readily implemented in implantable devices already having an appropriate signal sensed for other device functions and which may also be used for determining respiration parameters. Patients having such devices may receive greater benefit by the added detection of respiratory disturbances when they occur.

Signal data stored in memory 516 directly from A/D converter 515 may be uplinked to external device 532. As an alternative to performing respiratory disturbance detection online or in real time within internal device 510, stored signal data may be post-processed by external device 532. External device 532 is preferably a microprocessor-based device, which may be better able accommodate computationally-intensive algorithms than an implantable device for extracting respiration data from a sensed signal and for processing such data for the detection of pathologic patterns and for measuring characteristics of such patterns. External device 532 may be embodied as a "programmer," known for use with implantable, programmable devices for programming operational parameters into the internal device and for receiving stored data or other operational information from the implanted device. External device 532 may alternatively be in the form of a personal computer with an added telemetry interface for communicating with internal device 510. When embodied as a "programmer," external device 532 may receive stored signal data and save it in a format that may be transferred to a personal computer for further processing or by internet to a central patient management network. A bi-directional communication system that is network, Internet, intranet and worldwide web compatible to enable chronic monitoring based on data obtained from implantable monitors is generally disclosed in International Publication No. WO 01/70103 A2, issued to Webb et al, incorporated herein by reference in its entirety.

A respiration disturbance detector 538 may be included as an executable program in microprocessor 535 of external device 532. Detector 538 detects respiratory disturbances offline, using methods described herein, from stored signal data uplinked from internal device 510. If a pathologic breathing pattern is detected, a clinician alert 540 may be generated, which may be an audible and/or visual notification displayed on display 542 with supporting data. Metrics of detected disturbances are also preferably displayed on display 542.

When method 275 (FIG. 5) for determining a circulatory delay time is included in a system for monitoring respiratory disturbances in a patient with heart failure, an oximeter for measuring blood oxygen saturation may be provided as an implantable sensor or as an external sensor. Therefore an oximeter may be included in implanted sensors 500 and provide oxygen saturation data directly to internal device 510. An oxygen saturation signal may then be used in determining circulatory delay time in response to detecting a respiratory disturbance according to method 275. The oxygen saturation signal may additionally be the primary signal used by respiratory disturbance detector 514 for measuring the patient's respiration rate for detecting respiratory disturbances.

Alternatively, an external oximeter 530 may be provided for measuring blood oxygen saturation. An external oximeter may be placed at various body locations but is preferably placed on a fingertip or ear lobe. The oxygen saturation signal may be received by the external device 532 on signal line 534 and may under go filtering, amplification or other signal conditioning and digitization by sensor interface 536. Sensor interface 536 may be included in external device 532 or may be coupled between oximeter 530 and external device 532. The oxygen saturation signal from signal conditioning circuit 536 can be downlinked to internal device 510 via telemetry link 520 such that when internal device 510 detects a respiratory disturbance, the circulatory delay time may be determined according to method 275 described above, under the control of microprocessor 517.

Thus, a system and method have been described for monitoring respiration and detecting respiratory disturbances that are related to a pathological condition. While specific embodiments have been described herein, it is recognized that variations of the described methods for detecting respiratory disturbances, measuring characteristics of the disturbances, and storing and displaying respiratory disturbance data will exist. The embodiments described herein, therefore, are intended to be exemplary, not limiting, with regard to the following claims.

The invention claimed is:

1. A device for detecting a respiratory disturbance, comprising:
    means for sensing a physiological signal containing a frequency component or an amplitude component related to a common characteristic of at least two respiratory cycles;
    means for deriving at least one respiratory parameter from the physiologic signal;
    means for detecting a respiratory disturbance event when the at least one respiratory parameter meets or exceeds a predetermined criteria threshold for detecting the respiratory disturbance; and
    means for determining a circulatory delay time comprising means for measuring an oxygen saturation and means for determining a time between the respiratory disturbance and one of a subsequent minimum and a subsequent maximum oxygen saturation.

2. A device according to claim claim 1, further comprising means for measuring the magnitude of a characteristic of the respiratory disturbance.

3. A device according to claim 2 wherein the means for measuring the magnitude of a characteristic of the respiratory disturbance comprises means for measuring the magnitude of a characteristic of at least one of:
    an apnea duration;
    a hypopnea duration;
    a hyperpnea duration; and
    a periodic breathing cycle length.

4. A device according to claim 1, wherein the means for sensing a physiological signal comprises means for sensing at least one of is at least a one of:
    a thoracic impedance;
    an ECG signal;
    an EGM signal;
    a blood pressure signal;
    an activity level measurement; and
    an oxygen saturation measurement.

5. A device according to claim 1, wherein the means for detecting a respiratory disturbance comprises means for detecting Kussmaul breathing.

6. A device according to claim 1, wherein the means for detecting a respiratory disturbance comprises means for detecting a Cheyne-Stokes respiration event.

7. A device according to claim 1, wherein the means for detecting a respiratory disturbance comprises comprises means for detecting a sleep apnea event.

8. A device according to claim 1, further comprising means for determining an estimate of cardiac output based on the circulatory delay time.

9. A device according to claim 1, further comprising means for determining an estimate of cardiac function based on a metric of the respiratory disturbance.

10. A device according to claim 9, further comprising means for determining a heart failure status of a patient in the event that the estimate of cardiac function is lower than a predetermined lower threshold.

11. A device according to claim 1, further comprising means for triggering the storage of a physiological data item upon the detection of the respiratory disturbance.

12. A device according to claim 1, further comprising means for triggering a therapy based at least in part upon detection of the respiratory disturbance.

13. A device according to claim 1, further comprising means for generating a warning to alert a clinician or a patient of the detection of the respiratory disturbance.

14. A computer readable medium for storing a set of computer instructions for performing the following method, comprising:
   instructions for sensing a physiological signal containing a frequency component or an amplitude component related to a common characteristic of at least two respiratory cycles;
   instructions for deriving at least one respiratory parameter from the physiologic signal;
   instructions for detecting a respiratory disturbance event when the at least one respiratory parameter meets or exceeds a predetermined criteria threshold for detecting the respiratory disturbance; and
   instructions for determining a circulatory delay time comprising measuring an oxygen saturation and determining a time between the respiratory disturbance and a subsequent minimum or a subsequent maximum oxygen saturation.

15. A medium according to claim 14, further including:
   instructions for measuring the magnitude of a characteristic of the respiratory disturbance.

16. A medium according to claim 14, further comprising:
   instructions for determining an estimate of cardiac output based on the circulatory delay time.

17. A medium according to claim 16, further comprising instructions for determining a heart failure status of a patient in the event that the estimate of cardiac function is lower than a predetermined lower threshold.

18. A medium according to claim 14, further including instructions determining an estimate of cardiac function based on a metric of the respiratory disturbance.

19. A medium according to claim 14, further comprising instructions for triggering the storage of a physiological data item upon the detection of the respiratory disturbance.

20. A medium according to claim 14, further comprising instructions for triggering a therapy based at least in part upon detection of the respiratory disturbance.

21. A medium according to claim 14, further comprising instructions for generating a warning to alert a clinician or a patient of the detection of the respiratory disturbance.

* * * * *

UNITED STATES PATENT AND TRADEMARK OFFICE
CERTIFICATE OF CORRECTION

| | | |
|---|---|---|
| PATENT NO. | : 7,524,292 B2 | Page 1 of 1 |
| APPLICATION NO. | : 11/565092 | |
| DATED | : April 28, 2009 | |
| INVENTOR(S) | : Yong K. Cho et al. | |

It is certified that error appears in the above-identified patent and that said Letters Patent is hereby corrected as shown below:

Title page, inventors item (75) to read as follows: Yong K. Cho, Maple Grove, MN (US); Steven N. Lu, Fridley, MN (US); Luc R. Mongeon, Minneapolis, MN (US); Scott W. Davie, Saint Paul, MN (US); Todd J. Sheldon, North Oaks, MN (US); Mark K. Erickson, Brooklyn Park, MN (US); H. Toby Markowitz, Roseville, MN (US)

Signed and Sealed this
First Day of February, 2011

David J. Kappos
*Director of the United States Patent and Trademark Office*